United States Patent

Ito et al.

[11] Patent Number: 5,399,783
[45] Date of Patent: Mar. 21, 1995

[54] PREPARATION OF 6,6′-DIHYDROXY-3,3,3′,3′-TETRAMETHYL-1,1′-SPIROBIINDANE

[75] Inventors: Mizuo Ito; Shigeru Iimuro, both of Aichi, Japan

[73] Assignee: Mitsui Toatsu Chemicals, Inc., Tokyo, Japan

[21] Appl. No.: 225,559

[22] Filed: Apr. 11, 1994

[30] Foreign Application Priority Data

Apr. 12, 1993 [JP] Japan .................. 5-084412
Apr. 19, 1993 [JP] Japan .................. 5-091384

[51] Int. Cl.$^6$ .................................................. C07C 39/12
[52] U.S. Cl. .................................................. 568/719
[58] Field of Search .......................................... 568/719

[56] References Cited

U.S. PATENT DOCUMENTS 3,271,463  9/1966  Howard .............................. 568/719
4,605,789  9/1986  Silvis et al. ........................ 568/719

FOREIGN PATENT DOCUMENTS 62-4239   1/1987  Japan .
62-10030  1/1987  Japan .
62-42941  2/1987  Japan .
63-146837 6/1988  Japan .

OTHER PUBLICATIONS

Journal of Polymer Science, Part A, vol. 3, pp. 3209–3217 (1965).
Journal of Chemical Society, 1962, p. 415.

Primary Examiner—Werren B. Lone
Attorney, Agent, or Firm—Burns, Doane, Swecker & Mathis

[57] ABSTRACT

Crystals of 6,6′-dihydroxy-3,3,3′,3′-tetramethyl -1,1′-spirobiindane (hereinafter referred to as SPI) are obtained by cooling a phenol solution containing 6,6′-dihydroxy-3,3,3′,3′-tetramethyl-1,1′-spirobiindane when crystallization is started at a temperature higher than a transition temperature between SPI and an adduct of SPI with phenol. The crystals are washed with an organic solvent or contacted with water and further washed with an organic solvent. When crystallization is started at a temperature less than the transition temperature, adduct crystals of SPI with phenol are obtained from the phenol solution. Phenol is removed from the adduct crystals and the adduct crystals are contacted with water to obtain a hydrate and further the hydrate is washed with an organic solvent.

33 Claims, 2 Drawing Sheets

PREPARATION OF 6,6'-DIHYDROXY-3,3,3',3'-TETRAMETHYL-1,1'-SPIROBIINDANE

BACKGROUND OF THE INVENTION (a) Field of the Invention

The present invention relates to a process for preparing 6,6'-dihydroxy-3,3,3',3'-tetramethyl-1,1'-spirobiindane (hereinafter referred to as SPI) and an adduct of SPI with phenol. More particularly, it relates to (A) a process for preparing SPI of high purity by cooling a phenol solution of SPI prepared, for example, by heating 2,2-bis(4-hydroxyphenyl)propane (hereinafter referred to as bisphenol A) in the presence of an acid catalyst or by dissolving crude SPI crystals into phenol, to obtain SPI crystals, and (B) a process for preparing SPI of high purity by cooling the phenol solution of SPI to obtain an adduct of SPI with phenol, and removing phenol from the adduct.

(b) Description of the Prior Art

Known processes for preparing SPI are as follows:

(1) a process which comprises treating bisphenol A in the presence of water in sulfuric acid at a temperature of 140° C. and carrying out fractional crystallization from an organic solvent such as toluene to prepare SPI (U.S. Pat. No. 3,271,463);

(2) a process which comprises treating bisphenol A with concentrated hydrochloric acid in the presence of water at a temperature of 100° C. in an autoclave and carrying out fractional crystallization from an organic solvent such as toluene to prepare SPI (U.S. Pat. No. 3,271,463);

(3) a process which comprises heating bisphenol A in hydrobromic acid (Journal of Chemical Society, p415, 1962);and (4) a process which comprises heating bisphenol A in the presence of a perfluoroalkanesulfonic acid, an aliphatic sulfonic acid or an ultrastrongly acidic resin (JP-A-62-10030, JP-A-62-42941 and JP-A-62-4239).

However, the abovementioned processes are disadvantageous from a viewpoint that SPI crystals obtained are not as good as they are expected in purity and the crystals are needed to further purify. For examples, chloroform washing, converting SPI into a disodium salt of it, followed by four times of recrystallization, further converting the salt into free SPI and furthermore one time of recrystallization are needed in the purification step (journal of polymer Science: Part A by Stueben, Vol.3, pp3,209–3217, 1965).

Moreover, a method is known which comprises heating bisphenol A with methanesulfonic acid catalyst to obtain a reaction mixture, putting the reaction mixture into water to obtain a precipitate, washing the precipitate with methylene chloride, dissolving the precipitate in a mixed solvent containing methanol and methylene chloride, adding water into the solution to obtain a precipitate, and repeating the abovementioned treatments several times (JP-A-63-146837). In this method, a lot of solvents are used, the step for preparing SPI is large in number and its operation is complex.

SUMMARY OF THE INVENTION

The inventors of the present invention have attempted to solved the abovementioned problems by establishing processes for the advantageous preparation of SPI on an industrial scale.

We have found that (A) SPI crystals are crystals obtained by starting their crystallization at a temperature higher than a transition temperature between SPI and an adduct of SPI with phenol in a phenol solution of SPI, for example, a solution containing crude SPI and phenol or reaction mixture obtained by heating bisphenol A in the presence of an acid catalyst. When the crystallization is started after adding an organic solvent into a phenol solution of SPI, SPI crystals are obtained without being affected by the transition temperature between SPI and an adduct of SPI with phenol. These SPI crystals have a small amount of impurities. However, SPI of high purity is obtained by washing these SPI crystals with an organic solvent or contacting them with water to obtain a hydrate and washing the hydrate with an organic solvent.

We have also found that (B) adduct crystals of SPI and phenol are crystals obtained by starting their crystallization at a temperature less than a transition temperature between SPI and an adduct of SPI with phenol in a phenol solution of SPI, for example, a solution containing crude SPI and phenol or reaction mixture obtained by heating bisphenol A in the presence of an acid catalyst. These adduct crystals do not essentially contain impurities except phenol. SPI of high purity is obtained by removing phenol from these adduct crystals. Further SPI of ultrahighly purity is obtained by contacting the abovementioned SPI crystals with water to obtain a hydrate and washing the hydrate with an organic solvent.

Accordingly, one aspect of the present invention is a process for advantageously preparing SPI of high purity which comprises starting crystallization of SPI in a phenol solution of SPI at a temperature higher than a transition temperature between SPI and an adduct of SPI with phenol to obtain SPI crystals and washing the SPI crystals thus obtained with an organic solvent, or contacting SPI crystals obtained in the previous step with water to obtain a hydrate and washing the hydrate with an organic solvent.

Another aspect of the present invention is a process for advantageously preparing SPI of high purity which comprises starting crystallization of SPI in a phenol solution of SPI at a temperature less than a transition temperature between SPI and an adduct of SPI with phenol to make an adduct of SPI with phenol, removing phenol from the adduct, further contacting SPI crystals obtained in the previous step with water to obtain a hydrate and washing the hydrate with an organic solvent.

DETAILED DESCRIPTION OF THE INVENTION

Figure 1:
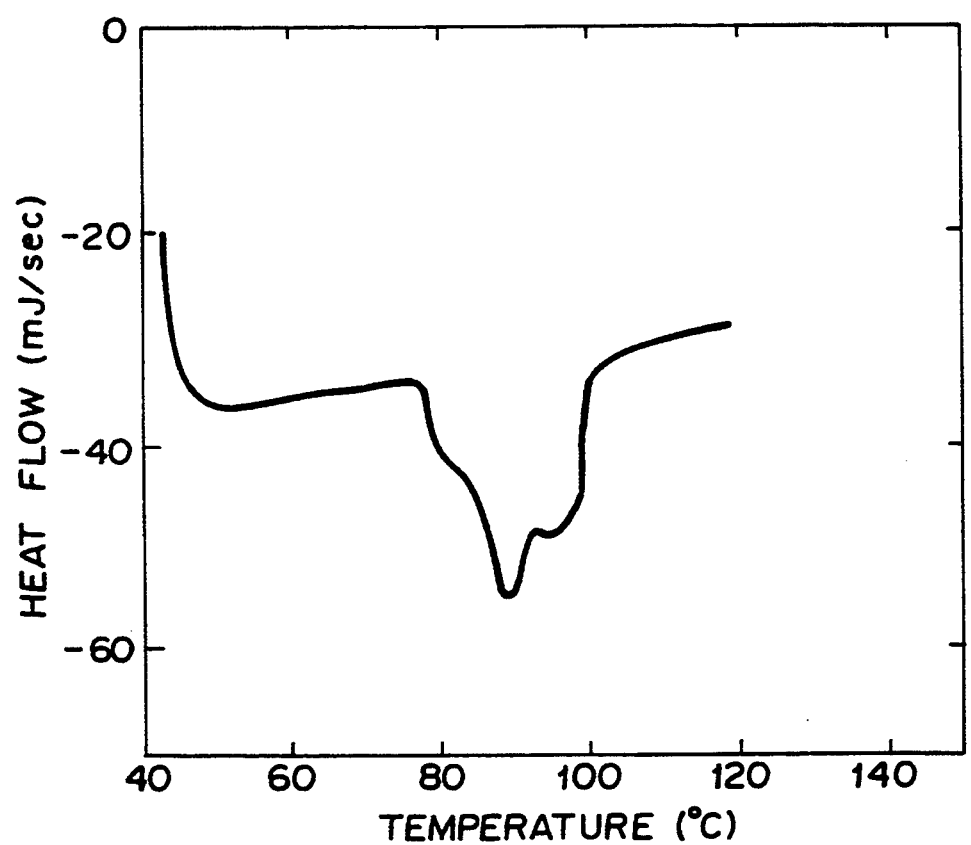
FIG. 1 is a differential scanning calorimeter chart (hereinafter referred to as DSC)of an adduct at a high temperature.

A phenol solution of SPI used in the present invention is obtained by treating bisphenol A in the presence of an acid catalyst. The acid catalyst includes, for example, sulfuric acid, hydrochloric acid, hydrobromoic acid, methanesulfonic acid, trifluoromethanesulfonic acid, an ultrastrongly acidic resin called Nafion of H type (produced by Du Pont Co. Ltd.) and so on, preferably methanesulfonic acid, trifluoromethanesulfonic acid, an ultrastrongly acidic resin called Nafion of H type (produced by Du Pont Co. Ltd.) and more preferably methanesulfonic acid and trifluoromethanesulfonic acid.

Heating is usually carried out in the range of 50° to 200° C. and heating period is usually in the range of 1 to 20 hours. Any of bisphenol A on sale on the market is sufficient as the raw material.

SPI in a reaction mixture is usually 10 to 45% by weight and the reaction mixture may become a phenol solution of SPI. The reaction mixture may be concentrated to be a phenol solution of SPI of 45 to 55% by weight. The concentration operation is usually carried out at a temperature of 100° to 150° C. under reduced pressure. A solution obtained by adding phenol to crude SPI of low purity to keep it in the range of 10 to 55% by weight may also be used as the phenol solution of SPI.

Another phenol solution of SPI used in the present invention is obtained by adding crude SPI into phenol and dissolving it. The crude SPI usually contains about 1 to 2% by weight of phenol and about 2% by weight of unknown impurities.

PREPARATION (A)

When a phenol solution of SPI is cooled down, the transition temperature between SPI and an adduct of SPI with phenol appears. The transition temperature is in the vicinity of 77° C. Seed crystals are usually added into the phenol solution at a temperature of 85° to 90° C. Crystals obtained from the phenol solution of SPI of other batches in advance may be used as the seed crystals. When crystallization is started keeping the phenol solution of SPI at a temperature higher than the transition temperature, SPI crystals are obtained. Even if the phenol solution is cooled down to a temperature less than the transition temperature, SPI crystals are also obtained. About 2 to 4 hours are usually needed to complete their crystallization.

The cooling temperature is affected by the concentration of SPI. The cooling may be carried out at a temperature of 30° to 70° C. However, at a temperature less than 30° C. the mother liquor may solidify or its mixing may become difficult owing to the increase of viscosity of a slurry. At a temperature more than 70° C. the solubility of SPI may increase and the yield of SPI may decrease.

When the viscosity of the slurry is too high, the slurry may be diluted with an organic solvent having a small degree of solubility of the abovementioned SPI. The organic solvent includes benzene, toluene, cyclohexane, methylene chloride, chloroform and so on. The organic solvent is not particularly limited in amount but is preferably employed to keep the slurry concentration in the range of 5 to 20% by weight in order to ease its operation. When the slurry is diluted, it can be cooled down to normal temperature and operations concerning the slurry may become easier.

When crystallization is started after adding an organic solvent into a phenol solution of SPI, SPI crystals are obtained without being affected by the transition temperature between SPI and an adduct of SPI with phenol. Benzene, toluene, cyclohexane, chloroform and so on are illustrated as the organic solvent having a small amount of solubility of SPI. The solvent may preferably be employed in an amount of 3% by weight or more. More preferably it may be employed in an amount of 5 to 50% by weight. In an amount less than 3% by weight, the crystals contain more phenol and the phenol has to be removed in the following steps. On the other hand, in an amount of 30% by weight or more the process may become inferior economically and the yield of SPI may also decrease. The amount just gives a result that the solvent has been employed in an amount more than it is needed.

When an organic solvent is added to the slurry, the solidification temperature of the mother liquor decreases. The slurry can be cooled down to normal temperature by adding the organic solvent in an amount of about 10% by weight of the slurry and it becomes easier to carry out operations concerning the slurry.

Methods including pressure filtration, absorbing filtration, centrifugal filtration and so on may be used to recover SPI crystals from the slurry and preferably centrifugal filtration is employed in the case. When the SPI crystals are washed with an organic solvent selected from the group consisting of benzene, toluene, cyclohexane, methylene chloride and chloroform to exclude the mother liquor sticking to the SPI crystals in case of its filtration, crude crystals having a higher purity are obtained.

The crude crystals usually contain a small amount of phenol (about 1 to 2% by weight) and unknown impurities (about 2% by weight) and organic solvent washing is illustrated as a method for removing them. An organic solvent having a small amount of solubility of SPI can be used as the organic solvent and the organic solvent includes benzene, toluene, methylene chloride, chloroform and so on and preferably benzene is employed. It may be employed at a weight ratio of an organic solvent to the crude crystals of 2:1 to 10:1. A mixture containing an organic solvent and the crude crystals is held at a temperature of 60° to 80° C. for 1 to 5 hours after adding the organic solvent, cooled and filtrated. The crystals obtained in the filtration step are dried at a temperature of 100° to 130° C. under reduced pressure.

In case that a more highly purified product is needed, crude crystals are contacted with water to obtain a hydrate of SPI and the hydrate is washed with an organic solvent to exclude its impurities. Recrystallization is not needed in this case. Water may be employed at a weight ratio of water to the crude crystals of 2:1 to 10:1. A mixture containing an organic solvent and the crude crystals is held at a temperature of normal temperature to 100° C. for 1 to 10 hours after adding the organic solvent, cooled and filtrated. The crystals obtained in the washing step are crystals of a hydrate and may be washed with an organic solvent having a small amount of solubility of SPI. The organic solvent includes benzene, toluene, chloroform, methylene chloride and so on and preferably benzene is employed. It may be employed at a weight ratio of an organic solvent to the hydrate of 2:1 to 10:1. A mixture containing an organic solvent and the hydrate is held at a temperature of 50° to 75° C. for 1 to 5 hours after adding the organic solvent, cooled and filtrated. The crystals obtained in the filtration step are dried at a temperature of 100° to 130° C. under reduced pressure.

PREPARATION (B)

A phenol solution of SPI has the transition temperature between SPI and an adduct of SPI with phenol and the transition temperature is in the vicinity of 77° C. The phenol solution of SPI is cooled down to a temperature less than the transition temperature keeping the state of super-saturated concentration of it. Seed crystals are usually added into the phenol solution at a temperature of about 75° C. Crystals obtained from the phenol solution of SPI of other batches in advance are may be used as the seed crystals. When crystallization is started at a temperature less than the transition temperature, an adduct is obtained at a molar ratio of SPI to phenol of 1. The cooling temperature is affected by the concentration of SPI. However the cooling may be conducted at a temperature of 30° C. to the transition temperature. At a temperature less than 30° C. , the mother liquor may solidify or its mixing may become difficult owing to the increase of viscosity of a slurry. At a higher temperature, the solubility of the adduct may increase and the yield of SPI may decrease.

When the viscosity of the slurry is too high, the slurry may be diluted with an organic solvent having a small degree of solubility of the abovementioned adduct. The organic solvent includes benzene, toluene, cyclohexane, methylene chloride, chloroform and so on. The organic solvent is not particularly limited in amount but is preferably employed to keep the slurry concentration in the range of 5 to 20% by weight in order to ease its operation. When the slurry is diluted, it can be cooled down to normal temperature and it may become easier to carry out operations concerning the slurry.

Methods including pressure filtration, absorbing filtration, centrifugal filtration and so on may be employed to recover adduct crystals from the slurry and preferably centrifugal filtration is employed in the case. When the adduct crystals are washed with an organic solvent selected from the group consisting of benzene, toluene, cyclohexane, methylene chloride and chloroform to exclude the mother liquor sticking to the adduct crystals in case of its filtration, adduct crystals having a higher purity are preferably obtained.

Methods including water washing, distillation, organic solvent washing and so on are illustrated as the method for removing phenol from the adduct crystals.

Water may be employed at a weight ratio of water to the adduct crystals of 3:1 to 10:1 and the slurry is held at a temperature of 80° to 100° C. for 2 to 5 hours in the method of water washing. The adduct crystals obtained in the filtration step are dried at a temperature of 100 to 130° C. under reduced pressure.

The temperature in a still is usually of 220° to 230° C. at a pressure of 10 to 20 mm Hg abs to exclude phenol in the method of distillation .

Benzene, toluene, methylene chloride, chloroform and so on are used as the organic solvent in the method of organic solvent washing and preferably benzene is used. The organic solvent may be employed at a weight ratio of an organic solvent to the adduct of 2:1 to 10:1. A mixture containing an organic solvent and the adduct crystals is held at a temperature of 70° to 80° C. for 2 to 5 hours after adding the organic solvent, cooled and filtrated. The adduct crystals obtained in the filtration step are dried at a temperature of 100° to 130° C. under reduced pressure.

In case that a more highly purified SPI is needed, SPI obtained in the abovementioned methods is contacted with water to obtain a hydrate of SPI and the hydrate is washed with an organic solvent to exclude its impurities. Recrystallization is not needed. Water may be employed at a weight ratio of water to the SPI of 2:1 to 10:1. A mixture containing water and the SPI is held at a temperature of normal temperature to 100° C. for 1 to 10 hours after adding water, cooled and filtrated. The SPI crystals obtained in the washing step are crystals of a hydrate and may be washed with an organic solvent having a small amount of solubility of SPI. The organic solvent includes benzene, toluene, chloroform, methylene chloride and so on and preferably benzene is employed. It may be employed at a weight ratio of an organic solvent to the hydrate of 2:1 to 10:1. A mixture containing an organic solvent and the hydrate is held at a temperature of 50° to 75° C. for 1 to 5 hours after adding the organic solvent, cooled and filtrated. The crystals obtained in the filtration step are dried at a temperature of 100° to 130° C. under reduced pressure. The adduct crystals obtained in the method of water washing may be washed with an organic solvent immediately after their filtration.

The present invention is illustrated in more detail by reference to the following examples.

EXAMPLE 1

A 1 liter volume separating flask was charged with 684 g (3.0 moles) of bisphenol A and 1.5 g of trifluoromethanesulfonic acid and reaction was carried out at 140° to 150° C. for 3 hours under stirring. After completing the reaction, the reaction mixture was cooled down to 90° C. A small amount of SPI crystals was added into the reaction mixture as the seed crystals and crystallization was started. The slurry was then cooled down to 30° C. for 3 hours to crystallize. Further 50 g of methylene chloride were added into the flask to decrease the viscosity of the slurry and further the slurry was cooled down to 20° C. for 1 hour. The slurry solution was then filtrated with a centrifugal filter and the cake of crystals was washed with methylene chloride of 20° C. under such conditions that the filter was working and methylene chloride was being sprinkled to obtain 220 g of crude crystals. The flask was charged with the crude crystals and 600 g of benzene and the crystals were washed at 75° C. for 3 hours under stirring. The slurry was then cooled down to normal temperature and filtrated with the filter. The cake of crystals was washed with benzene under such conditions that the filter was working and benzene was being sprinkled. After completing the wash, the cake thus obtained was dried at 130° C. for 3 hours under reduced pressure to obtain 196 g of crystals. Their melting point was 216° to 217° C. and their purity determined by liquid chromatography was 99.2% by weight.

EXAMPLE 2

A 1 liter volume separating flask was charged with 300 g of crude SPI ( SPI of 85% by weight, phenol of 2% by weight, unknown impurities of 13% by weight ) having a low purity and 400 g of phenol and the crude SPI was dissolved at 140° to 150° C. The solution was cooled down to 85° C. A small amount of SPI crystals was added to start crystallization. The solution was then cooled down to 30° C. for 3 hours to crystallize. Further 50 g of cyclohexane were added into the flask to decrease the viscosity of the slurry. Further the contents were cooled down to 20° C. for 1 hour. The slurry solution was then filtrated with a centrifugal filter and the cake of crystals was washed with cyclohexane of 20° C. under such conditions that the filter was working and cyclohexane was being sprinkled to obtain 215 g of crude crystals. The flask was charged with the crude crystals and 600 g of benzene and the crystals were washed at 75° C. for 3 hours under stirring. The slurry was then cooled down to normal temperature and filtrated with the filter. The cake of crystals was washed with benzene under such conditions that the filter was working and benzene was being sprinkled. After completing the wash, the cake thus obtained was dried at 130° C. for 3 hours under reduced pressure to obtain 194 g of crystals. Their melting point was 216° to 217° C. and their purity determined by liquid chromatography was 99.3% by weight.

EXAMPLE 3

A 1 liter volume separating flask was charged with 684 g (3.0 moles) of bisphenol A and 1.5 g of trifluoromethanesulfonic acid and reaction was carried out at 140° to 150° C. for 3 hours. After completing the reaction, the reaction mixture was cooled down to 100° C., 60 g of benzene were added into it, and the reaction mixture was cooled down to 70° C. A small amount of SPI crystals was added into the reaction mixture to start crystallization. The slurry was then cooled down to 20° C. for 3 hours to crystallize. Further, the slurry solution was filtrated with a centrifugal filter and the cake of crystals was washed with methylene chloride of 20° C. under such conditions that the filter was working and methylene chloride was being sprinkled to obtain 217 g of crude crystals. The flask was charged with the crude crystals and 600 g of benzene and the crystals were washed at 75° C. for 3 hours under stirring. The slurry was then cooled down to normal temperature and filtrated with the filter. The cake of crystals was washed with benzene under such conditions that the filter was working and benzene was being sprinkled. After completing the wash, the cake thus obtained was dried at 130° C. for 3 hours under reduced pressure to obtain 195 g of crystals. Their melting point was 216° to 217° C. and their purity determined by liquid chromatography was 99.2% by weight.

EXAMPLE 4

A 1 liter volume separating flask was charged with 200 g of crude crystals obtained in the same way as example 1 and 600 g of water and the slurry was then kept at 95° C. for 3 hours. The slurry was cooled down to 30° C. and filtrated with a centrifugal filter. The cake of crystals was washed with water of 30° C. under such conditions that the filter was working and water was being sprinkled. The flask was charged with the crystals having water and 600 g of benzene and the crystals were washed at 70° C. for 3 hours under stirring. The slurry was then cooled down to normal temperature and filtrated with the filter and the cake thus obtained was washed with benzene under such conditions that the filter was working and benzene was being sprinkled. After completing the wash, the cake thus obtained was dried at 130° C. for 3 hours under reduced pressure to obtain 194 g of crystals. Their melting point was 217° to 218° C. and their purity determined by liquid chromatography was 99.95% by weight.

EXAMPLE 5

A 1 liter volume separating flask was charged with 215 g of crude crystals obtained in the same way as example 2 and 600 g of water and the slurry was then kept at 95° C. for 3 hours. The slurry was cooled down to 30° C. and filtrated with a centrifugal filter. The cake of crystals was washed with water of 30° C. under such conditions that the filter was working and water was being sprinkled. The flask was charged with the crystals having water and 600 g of benzene and the crystals were washed at 70° C. for 3 hours under stirring. The slurry was then cooled down to normal temperature and filtrated with the filter and the cake thus obtained was washed with cyclohexane under such conditions that the filter was working and cyclohexane was being sprinkled. After completing the wash, the cake thus obtained was dried at 130° C. for 3 hours under reduced pressure to obtain 191 g of crystals. Their melting point was 217° to 218° C. and their purity determined by liquid chromatography was 99.95% by weight.

EXAMPLE 6

A 1 liter volume separating flask was charged with 684 g (3.0 moles) of bisphenol A and 1.5 g of trifluoromethanesulfonic acid and reaction was carried out at 140° to 150° C. for 3 hours under stirring. After completing the reaction, the reaction mixture was cooled down to 75° C. A small amount of SPI crystals was added into the reaction mixture as the seed crystals and crystallization was started. The slurry was then cooled down to 30° C. for 3 hours to crystallize. Further 50 g of methylene chloride were added into the flask to decrease the viscosity of the slurry and further the slurry was cooled down to 20° C. for 1 hour. The slurry solution was then filtrated with a centrifugal filter and the cake of crystals was washed with methylene chloride of 20° C. under such conditions that the filter was working and methylene chloride was being sprinkled to obtain 262 g of crystals having phenol. Their purity was 98.8% by weight in case that phenol was removed. The flask was charged with the crystals having phenol and 800 g of water and the crystals were washed at 95° C. for 3 hours under stirring. The slurry was then cooled down to 30° C. and filtrated with the filter. The cake of crystals was washed with water under such conditions that the filter was working and water was being sprinkled. After completing the wash, the cake thus obtained was dried at 130° C. for 3 hours under reduced pressure to obtain 195 g of crystals. Their melting point was 216° to 217° C. and their purity determined by liquid chromatography was 99.2% by weight.

Figure 2:
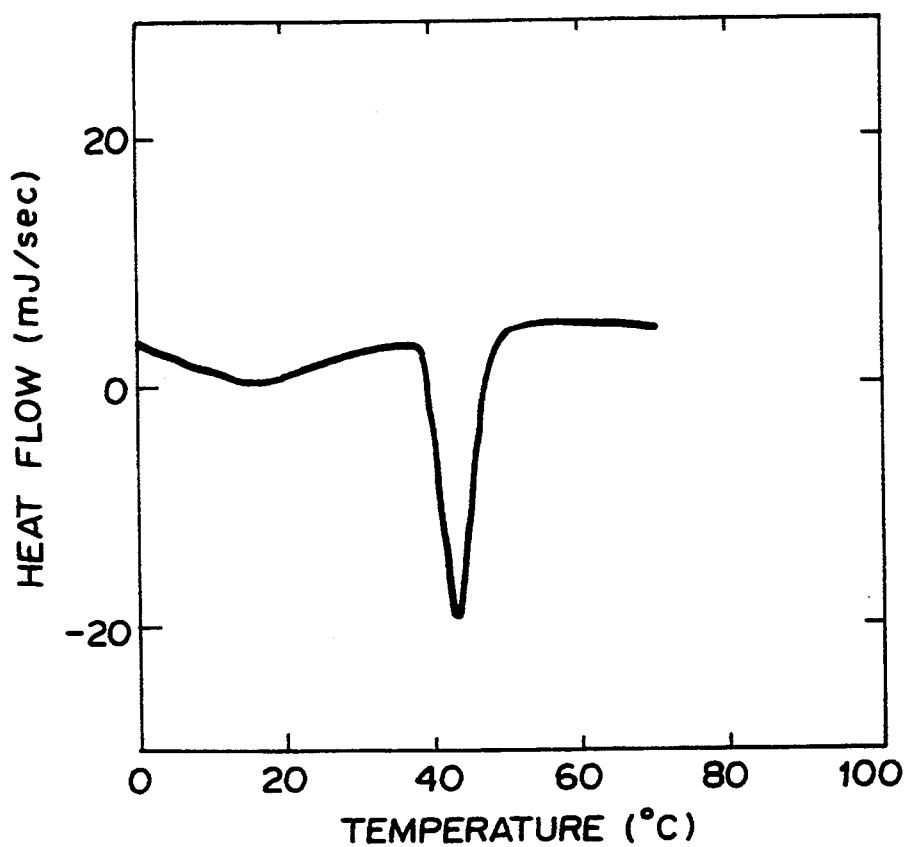
FIG. 2 is a DSC chart of a mixture of SPI and phenol at a low temperature.

According to the liquid chromatography, the composition of the crystals obtained in the abovementioned steps was such that SPI was 76.3% by weight and that phenol was 23.6% by weight. The crystals were determined with a DSC. The result is shown in FIG. 1. There was observed a peak value of endothermic change at 70° to 100° C. and the endothermic change seemed to depend on decomposition of an adduct. A mixture containing SPI and phenol was also determined with a DSC. The result is shown in FIG. 2. No peak value of endothermic change was observed and there was observed a peak value showing solution of phenol at 40° to 45° C.

According to the above results, it may be said that the thus-obtained crystals having phenol was adduct crystals having a molar ratio of SPI to phenol of 1:1.

Analytic conditions with DSC were as follows.

Instrument: a differential scanning calorimeter produced by Co. Rigaku

Conditions at low temperatures : in nitrogen atmosphere, rate of rising temperature=10° C. /min Conditions at high temperatures : in nitrogen atmosphere, rate of rising temperature=5° C. / min

EXAMPLE 7

A 1 liter volume separating flask was charged with 262 g of adduct crystals obtained in the same way as example 6 and the crystals were heated to melt at 190° C. Phenol was removed while reducing the inner pressure of the flask slowly. At the last stage of exclusion, the temperature and pressure were 225° C. and 10 mm Hg abs respectively and no exclusion of phenol was observed. The object thus obtained was 197 g, its melting point was 216° to 217° C. and its purity determined by liquid chromatography was 99.0% by weight.

EXAMPLE 8

A 1 liter volume separating flask was charged with 262 g of adduct crystals obtained in the same way as example 6 and 700 g of benzene were added into the flask. The slurry was treated at 75° to 80° C. for 2 hours, cooled down to 20° C. and filtrated with a centrifugal filter. The cake thus obtained was washed with benzene of 20° C. under such conditions that the filter was working and benzene was being sprinkled. After completing the wash, the cake thus obtained was dried at 130° C. for 3 hours under reduced pressure to obtain 190 g of crystals. Their melting point was 216° to 217° C. and their purity determined by liquid chromatography was 99.7% by weight.

EXAMPLE 9

A 1 liter volume separating flask was charged with 300 g of crude SPI ( SPI of 85% by weight, phenol of 2% by weight, unknown impurities of 13% by weight ) having a low purity and 300 g of phenol and the crude SPI was dissolved at 140° to 150° C. The solution was cooled down to 75° C. . A small amount of SPI crystals was added to start crystallization. The solution was then cooled down to 30° C. for 3 hours to crystallize. Further 50 g of cyclohexane were added into the flask to decrease the viscosity of the slurry. Further the contents were cooled down to 20° C. for 1 hour. The slurry solution was then filtrated with a centrifugal filter and the cake of crystals was washed with cyclohexane of 20° C. under such conditions that the filter was working and cyclohexane was being sprinkled to obtain 282 g of adduct crystals. Their purity was 98.9% by weight in case that phenol was removed. The flask was charged with the adduct crystals and 800 g of water and the slurry was treated at 95° C. for 3 hours under stirring. The slurry was then cooled down to 30° C. and filtrated with the filter. The cake of crystals was washed with water of 30° C. under such conditions that the filter was working and water was being sprinkled. After completing the wash, the cake thus obtained was dried at 130° C. for 3 hours under reduced pressure to obtain 207 g of crystals. Their melting point was 216° to 217° C. and their purity determined by liquid chromatography was 99.3% by weight.

EXAMPLE 10

SPI crystals having water (water content of 25% by weight) were obtained in the same treating way as example 6 but not dried yet. A 1 liter volume separating flask was charged with 261 g of the SPI crystals and 600 g of benzene and the crystals were washed at 75° C. for 3 hours under stirring. The slurry was then cooled down to normal temperature and filtrated with a centrifugal filter. The cake thus obtained was washed with benzene under such conditions that the filter was working and benzene was being sprinkled. After completing the wash, the cake thus obtained was dried at 130° C. for 3 hours under reduced pressure to obtain 189 g of crystals. Their melting point was 217° to 218° C. and their purity determined by liquid chromatography was 99.95% by weight.

EXAMPLE 11

Molten SPI was obtained in the same treating way as example 7 and phenol was removed therefrom. A 1 liter volume separating flask was charged with 600 g of water and 197 g of the molten SPI were added into the flask. The contents were kept at 95° C. for 1 hour, cooled down to normal temperature, and filtrated with a centrifugal filter. The flask was charged with the water containing crystals thus obtained and 600 g of benzene and the crystals were washed at 75° C. for 3 hours under stirring. The slurry was then cooled down to normal temperature to filtrate with the filter and the cake thus obtained was washed with methylene chloride under such conditions that the filter was working and methylene chloride was being sprinkled. After completing the wash, the cake thus obtained was dried at 130° C. for 3 hours under reduced pressure to obtain 191 g of crystals. Their melting point was 217° to 218° C. and their purity determined by liquid chromatography was 99.95% by weight.

EXAMPLE 12

SPI crystals having benzene (benzene content of 20% by weight) were obtained in the same treating way as example 8 but not dried yet. A 1 liter volume separating flask was charged with 237 g of the SPI crystals and 700 g of water. While removing benzene therefrom under stirring, the contents were raised up to 90° C. and kept at the temperature for 1 hour. The contents were then cooled down to normal temperature and filtrated with a centrifugal filter. The flask was charged with the water containing crystals thus obtained and 600 g of benzene and the crystals were washed at 75° C. for 3 hours under stirring. The slurry was then cooled down to normal temperature to filtrate with the filter and the cake thus obtained was washed with methylene chloride under such conditions that the filter was working and methylene chloride was being sprinkled. After completing the wash, the cake thus obtained was dried at 130° C. for 3 hours under reduced pressure to obtain 184 g of crystals. Their melting point was 217° to 218° C. and their purity determined by liquid chromatography was 99.97% by weight.

According to the present invention, SPI of high purity can be obtained in easy operations as mentioned by the above examples.

What is claimed is:

1. A process for preparing 6,6'-dihydroxy-3,3,3',3'-tetramethyl-1,1'-spirobiindane which comprises cooling a phenol solution containing 6,6'-dihydroxy-3,3,3',3'-tetramethyl-1,1'-spirobiindane to carry out crystallization, and recovering crystals comprising 6,6'-dihydroxy-3,3,3',3'-tetramethyl-1,1'-spirobiindane.

2. The process according to claim 1 wherein the crystallization is carried out by starting at a temperature higher than a transition temperature between 6,6'-dihydroxy-3,3,3',3'-tetramethyl-1,1'-spirobiindane and an adduct of 6,6'-dihydroxy-3,3,3',3'-tetramethyl-1,1'-spirobiindane with phenol.

3. The process according to claim 2 wherein the phenol solution is a reaction mixture obtained by heating 2,2-bis(4-hydroxyphenyl)propane in the presence of an acid catalyst.

4. The process according to claim 2 wherein the phenol solution is a solution obtained by dissolving crude 6,6'-dihydroxy-3,3,3',3'-tetramethyl-1,1'-spirobiindane in phenol.

5. A process for preparing 6,6'-dihydroxy-3,3,3',3'-tetramethyl-1,1'-spirobiindane which comprises cooling a solution to carry out crystallization, said solution being obtained by adding at least one organic solvent selected from the group consisting of benzene, toluene, cyclohexane, methylene choloride and chloroform into a reaction mixture obtained by heating 2,2-bis(4-hydroxyphenyl)propane in the presence of an acid catalyst, and recovering crystals comprising 6,6'-dihydroxy-3,3,3',3'-tetramethyl-1,1'-spirobiindane.

6. A process for preparing 6,6'-dihydroxy-3,3,3',3'-tetramethyl-1,1'-spirobiindane which comprises cooling a solution to carry out crystallization, said solution being obtained by dissolving crude 6,6'-dihydroxy-3,3,3',3'-tetramethyl-1,1'-spirobiindane in phenol and further adding thereinto at least one organic solvent selected from the group consisting of benzene, toluene, cyclohexane, methylene choloride and chloroform, and recovering crystals comprising 6,6'-dihydroxy-3,3,3',3'-tetramethyl-1,1'-spirobiindane.

7. The process according to claim 1, further comprising washing the recoverd crystals with at least one organic solvent selected from the group consisting of benzene, toluene, methylene choloride and chloroform.

8. The process according to claim 2, further comprising washing the recoverd crystals with at least one organic solvent selected from the group consisting of benzene, toluene, methylene choloride and chloroform.

9. The process according to claim 3, further comprising washing the recoverd crystals with at least one organic solvent selected from the group consisting of benzene, toluene, methylene choloride and chloroform.

10. The process according to claim 4, further comprising washing the recoverd crystals with at least one organic solvent selected from the group consisting of benzene, toluene, methylene choloride and chloroform.

11. The process according to claim 5, further comprising washing the recoverd crystals with at least one organic solvent selected from the group consisting of benzene, toluene, methylene choloride and chloroform.

12. The process according to claim 6, further comprising washing the recoverd crystals with at least one organic solvent selected from the group consisting of benzene, toluene, methylene choloride and chloroform.

13. The process according to claim 1, further comprising contacting the recoverd crystals with water and further washing the crystals with at least one organic solvent selected from the group consisting of benzene, toluene, methylene choloride and chloroform.

14. The process according to claim 2, further comprising contacting the recoverd crystals with water and further washing the crystals with at least one organic solvent selected from the group consisting of benzene, toluene, methylene choloride and chloroform.

15. The process according to claim 3, further comprising contacting the recoverd crystals with water and further washing the crystals with at least one organic solvent selected from the group consisting of benzene, toluene, methylene choloride and chloroform.

16. The process according to claim 4, further comprising contacting the recoverd crystals with water and further washing the crystals with at least one organic solvent selected from the group consisting of benzene, toluene, methylene choloride and chloroform.

17. The process according to claim 5, further comprising contacting the recoverd crystals with water and further washing the crystals with at least one organic solvent selected from the group consisting of benzene, toluene, methylene choloride and chloroform.

18. The process according to claim 6, further comprising contacting the recoverd crystals with water and further washing the crystals with at least one organic solvent selected from the group consisting of benzene, toluene, methylene choloride and chloroform.

19. The process according to claim 1 wherein the crystallization is carried out by starting at a temperature less than a transition temperature between 6,6'-dihydroxy-3,3,3',3'-tetramethyl-1,1'-spirobiindane and an adduct of 6,6'-dihydroxy-3,3,3',3'-tetramethyl-1,1'-spirobiindane with phenol to obtain an adduct of 6,6'-dihydroxy-3,3,3',3'-tetramethyl-1,1'-spirobiindane with phenol, and further removing phenol from the adduct.

20. The process according to claim 19 wherein the phenol solution is a reaction mixture obtained by heating 2,2-bis(4-hydroxyphenyl)propane in the presence of an acid catalyst.

21. The process according to claim 19 wherein the phenol solution is a solution obtained by dissolving crude 6,6'-dihydroxy-3,3,3',3'-tetramethyl-1,1'-spirobiindane in phenol.

22. The process according to claim 20, further comprising washing the resulting adduct with water to exclude phenol and obtain a hydrate.

23. The process according to claim 21, further comprising washing the resulting adduct with water to exclude phenol and obtain a hydrate.

24. The process according to claim 20, further comprising removing phenol from the resulting adduct by distillation.

25. The process according to claim 21, further comprising removing phenol from the resulting adduct by distillation.

26. The process according to claim 20, further comprising washing the resulting adduct with an organic solvent to exclude phenol.

27. The process according to claim 21, further comprising washing the resulting adduct with an organic solvent to exclude phenol.

28. The process according to claim 22, further comprising washing the resulting hydrate with an organic solvent.

29. The process according to claim 23, further comprising washing the resulting hydrate with an organic solvent.

30. The process according to claim 24, further comprising adding water to the resulting 6,6'-dihydroxy-3,3,3',3'-tetramethyl-1,1'-spirobiindane to obtain a hydrate, and further washing it with an organic solvent.

31. The process according to claim 25, further comprising adding water to the resulting 6,6'-dihydroxy-3,3,3',3'-tetramethyl-1,1'-spirobiindane to obtain a hydrate, and further washing it with an organic solvent.

32. The process according to claim 26, further comprising adding water to the resulting 6,6'-dihydroxy-3,3,3',3'-tetramethyl-1,1'-spirobiindane to obtain a hydrate, and further washing it with an organic solvent.

33. The process according to claim 27, further comprising adding water to the resulting 6,6'-dihydroxy-3,3,3',3'-tetramethyl-1,1'-spirobiindane to obtain a hydrate, and further washing it with an organic solvent.

* * * * *